(12) United States Patent
Nishimura (10) Patent No.: US 11,660,248 B2
(45) Date of Patent: May 30, 2023

(54) ELECTRIC MASSAGE INSTRUMENT

(71) Applicant: TRUSTLEX INC., Suita (JP)

(72) Inventor: Junichi Nishimura, Suita (JP)

(73) Assignee: TRUSTLEX INC., Suita (JP)

( * ) Notice: Subject to any disclaimer, the term of this patent is extended or adjusted under 35 U.S.C. 154(b) by 572 days.

(21) Appl. No.: 16/749,214

(22) Filed: Jan. 22, 2020

(65) Prior Publication Data

US 2020/0230018 A1 Jul. 23, 2020

(30) Foreign Application Priority Data

Jan. 23, 2019 (JP) .............................. JP2019-009646

(51) Int. Cl.
*A61H 13/00* (2006.01)
*A61H 23/02* (2006.01)
*A61N 5/06* (2006.01)

(52) U.S. Cl.
CPC .......... *A61H 13/00* (2013.01); *A61H 23/0245* (2013.01); *A61N 5/0603* (2013.01); *A61N 5/0625* (2013.01); *A61H 2201/0188* (2013.01); *A61H 2201/0207* (2013.01); *A61H 2201/10* (2013.01); *A61H 2201/1695* (2013.01); *A61N 2005/0606* (2013.01); *A61N 2005/0626* (2013.01); *A61N 2005/0659* (2013.01)

(58) Field of Classification Search
CPC .. A61H 13/00; A61H 23/0245; A61N 5/0603; A61N 5/0625
See application file for complete search history.

(56) References Cited

FOREIGN PATENT DOCUMENTS

| JP | S63-11176 A | 1/1988 |
| JP | 2003-24403 A | 1/2003 |
| JP | 2006-326426 A | 12/2006 |
| JP | 4204416 B2 | 1/2009 |
| JP | 2017-153829 A | 9/2017 |
| KR | 10-2010-0009670 A | 1/2010 |

*Primary Examiner* — John P Lacyk
(74) *Attorney, Agent, or Firm* — Manabu Kanesaka (57) ABSTRACT

An electric massage instrument can efficiently and easily control ultrasonic vibration function and infrared irradiation function to be simultaneously applied to a desired part. A single circuit board on which an electronic circuit having an ultrasonic vibration function and an infrared irradiation function is arranged in a gripping part gripped by hand, and irradiation parts of the infrared radiation function are provided on the contact part side of the tip end arranged to extend the circuit board. A housing forming a gripping part and a contact part is a single continuous housing made of synthetic resin, and the single circuit board extending to the tip end is fitted and fixed.

4 Claims, 5 Drawing Sheets

ELECTRIC MASSAGE INSTRUMENT

RELATED APPLICATIONS

The present application is based on, and claims priorities from, Japanese Applications No. 2019-009646 filed Jan. 23, 2019; and No. 2019-106225 filed Jun. 23, 2019, the disclosure of which is hereby incorporated by reference herein in its entirety.

TECHNICAL FIELD

The present invention relates to an electric massage instrument for massaging by contacting with a face, a neck, limbs, or in an oral cavity.

BACKGROUND ART

As a conventional massage instrument, for example, it is known that a massage instrument for an oral cavity which a brush attached to a tip end of a toothbrush is rotated by an electric motor or which is massaged in the oral cavity by an ultrasonic vibration through a brush bristle.

However, the conventional massage instrument configured as described above has a drawback that gums and a gingiva are damaged by a strong rotation of the brush. In addition, in the case of applying the ultrasonic vibration through the brush bristle, there is a drawback that the ultrasonic vibration cannot be effectively transmitted to the gums and the gingiva.

For this reason, Patent Literature 1 discloses an ultrasonic massage instrument for the gums which an oscillator and a power source are mounted in a cylindrical body, a switch for operating the oscillator is mounted in the cylindrical body, a piezoelectric vibrator is embedded inside of a tip end of a contact part formed elongated from the cylindrical body, a flexible material is attached around the tip end of the contact part in which the piezoelectric vibrator is buried, an oscillation output is applied to the piezoelectric vibrator from the oscillator, and the gums and a gingiva are massaged by transmitting an ultrasonic vibration generated from the piezoelectric vibrator through the flexible material.

Patent Literature 2 discloses an ultrasonic oral hygiene device comprising an ultrasonic irradiation part incorporating a cylindrical ultrasonic vibrator, a contact part integrally formed with the irradiation part, a switching circuit incorporated in the contact part connected to the ultrasonic vibrator, an oscillator connected to the switching circuit and sequentially outputting an output of a frequency for generating a radial vibration, a thickness vibration, and a longitudinal vibration of the ultrasonic vibrator, and a power source supplying power to the oscillator and an oscillation output from the oscillator generates the radial vibration, the thickness vibration and the longitudinal vibration corresponding to the frequency from the ultrasonic vibrator to clean an oral cavity and remove a plaque.

Patent Literature 3 discloses an electric massage instrument for gums comprising a massage contact part 2 (2a) provided continuously with a support column 4 in a chevron shape having a massage part 5 in a streamlined shape at the tip end in an electric massage instrument body 1 having a function of generating a power-driven vibration and an ultrasonic vibration, wherein the massage part is made of a low elastic modulus material such as natural rubber, synthetic rubber or silicone rubber having flexibility. In addition, Patent Literature 4 discloses a massage tool which uses a far-infrared ray.

Patent Literature 5 (paragraphs 0012, 0014, FIGS. 2 to 4(a) and 4(b)) discloses a massage instrument for an oral cavity comprising a contact part 5 having a vibration function for applying an ultrasonic vibration and an infrared irradiation function for irradiating an infrared ray to the gums, circuit boards 23, 4A having an ultrasonic function and an infrared irradiation function is arranged in a main body part 2 gripped by a hand and an irradiation part 51 having a far-infrared irradiation function is provided on a tip end side of the contact part 5 arranged to extend the circuit boards 23, 4A (FIG. 3-FIG. 4). However, a single circuit board configured with an electronic circuit having the ultrasonic vibration function and the infrared irradiation function is not arranged (the circuit boards 23 and 4A are separated), and the contact part has no projections and recesses and is not covered with a cap.

Patent Literature 6 (paragraphs 0001-0004, 0018, 0020-0055, FIGS. 2 to 6) discloses a massage instrument for an oral cavity comprising a contact part 10 having a vibration function for applying an ultrasonic vibration and an infrared irradiation function for irradiating an infrared ray to an affected part of the oral cavity such as gums, an electronic circuit having an ultrasonic function and an infrared irradiation function is arranged in a main body part 2 to grip with a hand, and an irradiation unit having an infrared irradiation function is provided on a tip end side of a gripping part. However, a single circuit board configured with an electronic circuit having the ultrasonic vibration function and the infrared irradiation functions is not arranged (the circuit boards 23 and 4A are separated), and the contact part has no projections and recesses and is not covered with a cap.

PATENT LITERATURE

Patent Literature 1: Japanese Patent Application Laid-Open No. 2003-24403
Patent Literature 2: Japanese Patent No. 4204416
Patent Literature 3: Japanese Patent Application Laid-Open No. 2006-326426
Patent Literature 4: Japanese Patent Application Laid-Open No. S63-11176
Patent Literature 5: Japanese Patent Application Laid-Open No. 2017-153829
Patent literature 6: Korean Patent Application Laid-Open No. 10-2010-0009670

DISCLOSURE OF INVENTION

Problems to be Solved by the Invention

By the way, it is known that it is effective to promote the secretion of saliva by massaging the oral cavity for the prevention of periodontal disease. This is because saliva protects the oral environment and performs many functions such as cleaning and antibacterial effects.

In this regard, according to the research of the present inventor, if a lot of saliva can be secreted efficiently and comfortably, not only periodontal disease can be prevented, but also the oral antioxidant effect, the antibacterial effect, and the bad breath prevention effect are exhibited. Furthermore, it has been found that the brain can be activated, and the role of accelerating the circulation of bodily fluid and improving the circulation of extra lymph can be performed.

However, as in conventional patent literatures, a vibration such as an ultrasonic vibration is not always enough to stimulate the oral cavity and effectively secrete saliva. For example, when saliva is secreted, the use of the brush described above is not only painful, but also not preferable for efficiently and stably secreting saliva.

Further, in the irradiation with a far-infrared ray or the like, the irradiation in only one direction is not preferable because the irradiation range is limited.

In addition, in the conventional patent literatures, it is not always enough to perform the massage hygienically even though it is necessary to be performed hygienically in order to massage in the oral cavity. More hygienic and safer device is required especially when a device is brought into contact with the tongue.

Patent Literatures 4 and 5 disclose a technique that exerts a thermal effect by the irradiation of the far-infrared ray on the affected part of the oral cavity. However, the far-infrared ray is absorbed by any substance and have the property which do not pass through. Therefore, the far-infrared ray does not irradiate the infrared ray to the deep part of the oral cavity. And, the irradiation in only one direction is not preferable because the irradiation range is limited. In addition, the single circuit board configured with the electronic circuit having the ultrasonic vibration function and the infrared irradiation function is not arranged (the circuit boards 23 and 4A are separated), and it can be said that a structure which suppresses the vibration by gripping the gripping part or transmit the vibration strongly to the tip end by loosening the gripping force is not employed.

According to the study of the present inventor, it has been found that the periodontal disease can be prevented, the brain can be activated and the role of accelerating the circulation of bodily fluid and improving the circulation of excess lymph can be performed if a lot of saliva can be efficiently secreted by applying the ultrasonic vibration to the tongue.

On the other hand, applying the ultrasonic vibration and the infrared irradiation is suitable not only in the oral cavity, but also for relaxation of the muscles of the body, such as the face, neck, and limbs, and for elimination of stiffness. It is required to be performed efficiently, and it is ideal that the vibration and the infrared effect can be easily controlled by hand.

Accordingly, the object of the present invention is to provide an electric massage instrument capable of efficiently and easily controlling the ultrasonic vibration function and the infrared irradiation function to be simultaneously applied to a desired part and capable of being used hygienically.

Means for Solving the Problem

In order to solve the above problem, the present invention is an electric massage instrument comprising a contact part having an ultrasonic vibration function to be applied an ultrasonic vibration and an infrared irradiation function to be irradiated an infrared ray by contacting an face, an neck, limbs, or contacting with an affected part of an oral cavity such as gums, a gingiva, and a tongue, and a circuit board configured with an electronic circuit having an ultrasonic vibration function and an infrared function in a main body part gripped by a hand, and an irradiation part of the infrared irradiation function is provided in the contact part on a tip end side arranged to extend the circuit board, the contact part is made of a member having infrared transparency and/or is provided with a cap which covers the contact part and the cap is made of a member having infrared transparency, the infrared irradiation function is a far-infrared function and a near-infrared irradiation function, and the circuit board is provided with a switching means which irradiates the far-infrared irradiation and the near-infrared irradiation simultaneously or individually.

The infrared ray to be irradiated include the far-infrared ray and the near-infrared ray. The far-infrared ray are electromagnetic waves having a wavelength of about 4-1000 μm and have properties close to radio waves, a thermal effect can be expected due to the property it does not permeate most of the substances and is absorbed and converted into heat. The near-infrared ray are electromagnetic wave having a wavelength of about 0.7-2.5 μm and have a wavelength close to that of red visible light, and since it has higher transparency than the far-infrared ray, it can be irradiated to a subcutaneous deep part of a desired part.

According to the present invention, the circuit board is a circuit board arranged to extend from the gripping part into the contact part, and a circuit board configured with the electric circuit having the ultrasonic vibration function and the infrared function is arranged to extend into the contact part, the vibration can be suppressed or conversely strengthened by controlling the force of gripping with the hand, so that the propagation of the vibration without loss of the ultrasonic vibration and its control can be performed, and the infrared ray irradiated simultaneously the vibration are irradiated to be scattered by the ultrasonic vibrations, and the desired part can be effectively and widely massaged. In addition, since the circuit board is covered with the single housing, the vibration of the circuit board is transmitted to the entire housing (any housing part), the vibration of the contact part can be increased or decreased by the force of gripping the housing.

The present invention is An electric massage instrument comprising a contact part having an ultrasonic vibration function to be applied an ultrasonic vibration and an infrared irradiation function to be irradiated an infrared ray by contacting an face, an neck, limbs, or contacting with an affected part of an oral cavity such as gums, a gingiva, and a tongue, and a circuit board configured with an electronic circuit having the ultrasonic vibration function and an infrared function in a main body part gripped by a hand, and an irradiation part of the infrared irradiation function is provided in the contact part on a tip end side arranged to extend the circuit board, the contact part is made of a member having infrared transparency and/or is provided with a cap which covers the contact part and the cap is made of a member having infrared transparency, the contact part or the cap is formed with a recess-projection shape except a brush made of rubber or synthetic resin, an irradiation by the infrared irradiation function is irradiated toward a position of the recess-projection shape except a brush made of rubber or synthetic resin, and on the tip side, the irradiation part of a far-infrared irradiation function and the irradiation part of a near-infrared irradiation function between the irradiation part of the far-infrared irradiation function are provided in the contact part or the irradiation part of the far-infrared irradiation function and the irradiation part of the far-infrared irradiation function are provided such that their directions are alternately changed.

According to the present invention, it is preferable that the size of the projection part of the recess-projection shape (except the brush) is 1 mm to 10 mm in diameter. Since the recess-projection shape (except the brush) is formed, the contact with the desired part is not a surface but a point, so that a more effective massage effect can be expected. Note that the recess-projection shape excludes a brush. This is because the brush damages the gums and tongue when used in the oral cavity. In addition, by constituting the cap by a member having higher flexibility than a member constituting the contact part (the housing of the massage instrument body) and is a member having infrared transparency and having a high thermal conductivity (heat radiation rubber and heat radiation silicone rubber processed products are suitable), it is easy to attach and detach, ensures hygienic use, and can exert a thermal effect by the infrared irradiation on the desired part.

In addition, the present invention is An electric massage instrument comprising a contact part having an ultrasonic vibration function to be applied an ultrasonic vibration and an infrared irradiation function to be irradiated an infrared ray by contacting an face, an neck, limbs, or contacting with an affected part of an oral cavity such as gums, a gingiva, and a tongue, and a circuit board configured with an electronic circuit having the ultrasonic vibration function and an infrared function in a main body part gripped by a hand, and an irradiation part of the infrared irradiation function is provided in the contact part on a tip end side arranged to extend the circuit board, the contact part is made of a member having infrared transparency and/or is provided with a cap which covers the contact part and the cap is made of a member having infrared transparency, the contact part and/or cape is formed with a thick part except the recess-projection shape and a thin part, and the recess-projection shape except the brush is not formed on the thin part, and the irradiation of the far-infrared function and the near-infrared function are irradiated toward the position of the thin part.

According to the present invention, the infrared irradiation function can irradiate the desired part regardless of the material of the contact part or the cap.

The cap is made of a synthetic resin or rubber that is more flexible than the contact part, and the inner diameter of the cap is narrower than the contact part, so that the housing is pressed against the circuit board. It is a structure that generates pressure.

According to the present invention, the cap squeezes the housing to contact the circuit board, so that a vibration of the circuit board is sufficiently transmitted to the contact part and the cap.

The present invention is the electric massage instrument, wherein a housing is provided to continuously have the contact part and a gripping part to be gripped by a hand, and the circuit board is a single board extended from the gripping part into the contact part, and an ultrasonic transducer for applying the ultrasonic vibrations is provided on the gripping part side of the circuit board, and the irradiation part of the infrared irradiation function is provided on the contact part side on the circuit board.

According to the present invention, since the ultrasonic transducer is provided on the gripping part of the circuit board, the ultrasonic vibration can be controlled with the strength of gripping, and thereby the area of the infrared irradiation can also be controlled. That is, by gripping the gripping part strongly, the ultrasonic vibration can be weakened, and the area of the infrared irradiation can be narrowed, and by gripping weakly, the ultrasonic vibration can be strong, and the area of the infrared irradiation can be widened.

In addition, the present invention is the electric massage instrument, wherein the housing is a housing comprising a front side case and a back side case which fit and fix the single circuit board, the single circuit board is fitted and fixed without a gap at the contact part of at least one of the front side case and back side case of the housing, the ultrasonic transducer of the single circuit board vibrates in a direction at least to the front face side case and the back side case.

According to the present invention, since the housing and the circuit board are fitted without the gap at the contact part of the massage instrument, it can be a structure that the ultrasonic vibration propagating without loss by the single circuit board is further transmitted to the desired part.

The present invention is the electric massage instrument, wherein the housing is a housing comprising a front side case and a back side case which fit and fix the single circuit board, a positioning member which connects the front side case and the back side case in the contact part is provided so as to penetrate the single circuit board, the positioning member contacts and transmit the vibration to the front side case and the back side case of the housing According to the present invention, the positioning member can sufficiently transmit the ultrasonic vibration from the circuit board to the front side and the back side of the housing.

The present invention is the electric massage instrument, wherein the housing is a housing comprising a front side case and the back side case which fit and fix the single circuit board, the contact part side of the single circuit board is fitted and fixed without a gap at least one of the front side case and back side case at the contact part of the housing, and a vibration transmitting part 8 is provided which stands up from the circuit board and contact at least the other of the front side case and back side case and transmits the vibration.

According to the present invention, the vibration transmitting part which transmits the vibration from single circuit board to the contact part of the housing is provided, and the ultrasonic vibration from the circuit board can be sufficiently transmitted to the contact part of the housing. Since the circuit board is covered with the single housing, the vibration of the circuit board is transmitted to the entire housing (any housing part), the vibration can be increased or decreased by the force of gripping the housing.

The present invention is the electric massage instrument, wherein in the contact part of the housing, since one of the front side case and the back side case is a frat part which the single circuit board is placed and the other of the front side case and the back side case cover the single circuit board in a cross-sectionally recessed shape so as to fit and fix without a gap.

According to the present invention, in the contact part of the housing, since one of the front side case and the back side case is a frat part which the single circuit board is placed in the contact part of the housing and the other of the front side case and the back side case cover the single circuit board in a cross-sectionally recessed shape, the one of the front side case and the back side case and the single circuit board can be fitted and fixed without the gap, the ultrasonic vibration propagating without loss by the single circuit board can be further transmitted to the desired part.

The present invention is the electric massage instrument, wherein the irradiation part of the infrared irradiation function is arranged on the front and back surface of the contact part of the single circuit board.

According to the present invention, an efficient vibration and infrared irradiation can be performed without changing a direction of the ultrasonic vibration or the infrared irradiation (there is no need to use the contact part upside down). As an example of use, it is suitable for use on the gums and inside the cheeks in the oral cavity, and for use under the armpits and the inside the knees.

The present invention is the electric massage instrument, wherein the housing and the single circuit board control the vibration transmitted from the contact part by adjusting the strength of gripping the gripping part of the housing by adjusting the condition of the contact via an adhesive agent on the gripping part side.

According to the present invention, the housing and the single circuit board can control the vibration transmitted from the contact part by adjusting the strength of gripping the gripping part of the housing by adjusting the condition of the contact via an adhesive agent on the gripping part side.

The present invention is the electric massage instrument, wherein a battery housing part is provided on the gripping part side of the back side case, and the gripping part side of the single circuit board is fixed to an upper part of the battery housing part.

According to the present invention, the battery housing part is provided in the gripping part side of the back side case, and the gripping part side of the single circuit board can be fixed to the upper part of the battery housing part.

Advantageous Effect of the Invention

According to the present invention, the electronic element having the ultrasonic vibration function is mounted on the circuit board, and the electronic element having the infrared irradiation function is also mounted on the circuit board. In addition, in the neck, limbs, and the oral cavity, massage can be performed efficiently and easily while adjusting with the gripping force of the hand.

Further, for an example of the use in the oral cavity, according to the present invention, the contact part has a flexibility and a removable cap is attached to perform massage, so that the contact part and the cap can be easily cleaned. Thus, it can be used hygienically and can be used without damaging the oral cavity.

BRIEF DESCRIPTION OF THE DRAWINGS

FIGS. 7(a) and 7(b) are views showing the cap of the electric massage instrument, wherein

DETAILED DESCRIPTION OF THE INVENTION

Hereinafter, specific embodiments for carrying out the present invention will be described with reference to the drawings.

First Embodiment

As shown in FIGS. 1 to 4(a) and (b), an electric massage instrument 1 of the present embodiment comprises a housing 2 including a gripping part 2b to be gripped by a hand and a contact part 2a to be applied to a face, a neck, limbs, and an oral cavity. The gripping part 2b is configured by fitting a plastic front side case 12A and a back side case 12B. Further, a battery housing part 12g is provided on the gripping part side of the back side case 12B and is covered with a battery cover 12C for taking in and out the battery G.

Figure 1:
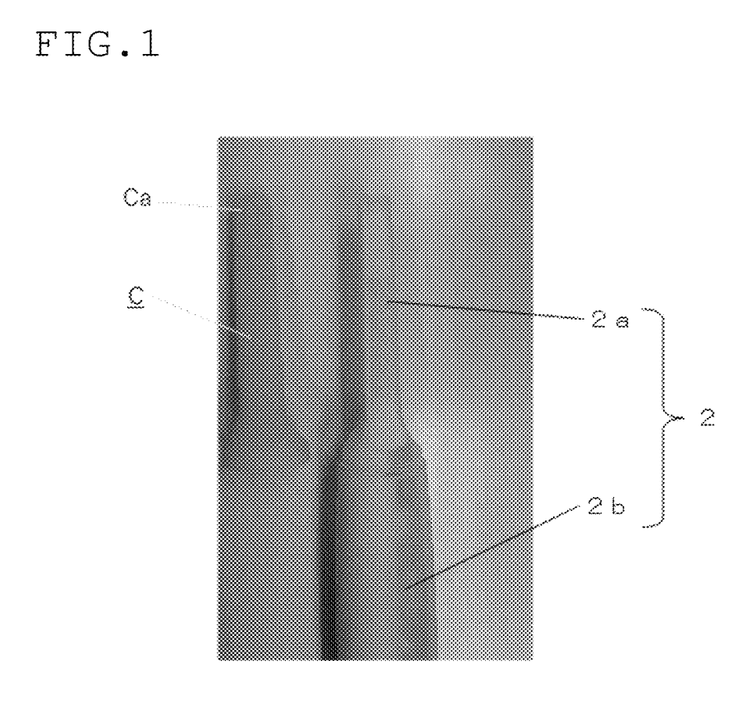
FIG. 1 is a perspective view showing an electric massage instrument from the front side according to a first embodiment of the present invention.

The gripping part 2b of the front side case 12A is provided with a switch button 12D for vibrating the contact part 2a or irradiating an infrared ray, and 12D is connected to a power switch 9 on a circuit board. A direction of the switch button 12D and an irradiation direction of the near-infrared irradiation function are set to the same direction.

Moreover, although the gripping part 2b is cylindrical shape so that it may be easy to grip with a hand, a cross section may be polygonal shape or rectangular shape like the contact part 2a.

The front side case 12A and the back side case 12B are fitted together on the upper side and the lower side, and a part from the gripping part 2b to the contact part 2a is configured as a single housing 2, and a single circuit board 6 is provided in the center of the inside of the housing 2, and is arranged with the length extending to the contact part 2a. The housing 2 is made of a transparent/semi-transparent synthetic resin, and an extension part 6a of a single circuit board is provided inside the back side case 12B and connected with a synthetic resin material covering the battery loaded in the back side case 12B. one of the front side case and back side case is a frat part which the single circuit board 6 is placed in the contact part 2a of the housing 2. The thickness of the circuit board 6 is formed to be thicker than the thickness of the back side case 12B on the contact part side. Further, the gripping part side of the single circuit board is fixed to an upper part of the battery housing part.

Figure 8:
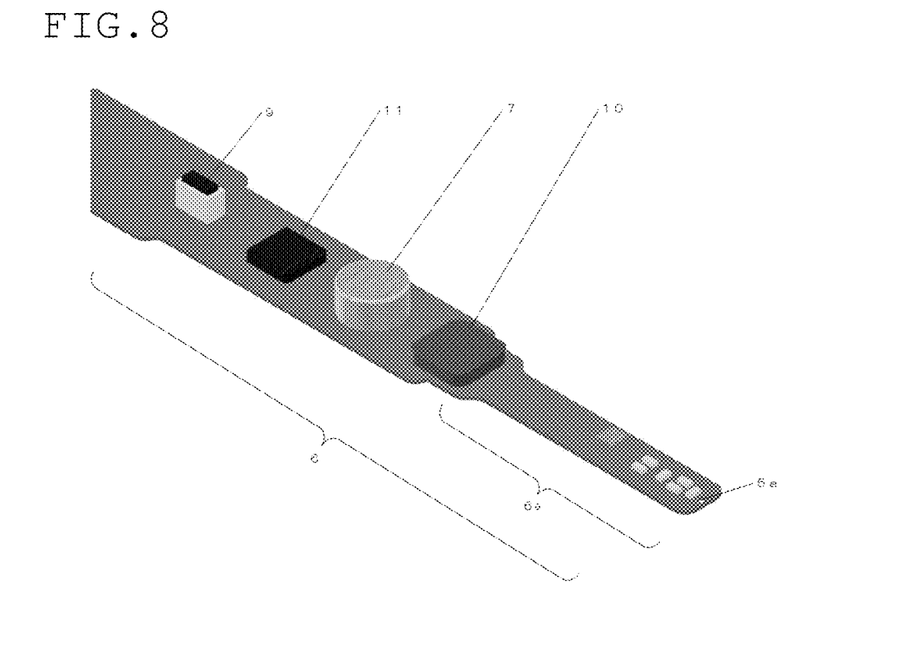
FIG. 8 is a perspective view showing an electric massage instrument according to a second embodiment of the present invention.

In addition, the housing 2 and the single circuit board 6 are fitted and fixed without a gap so as to prevent a loss of a vibration in the contact part 2a, and the housing and the circuit board are fixed via an adhesive agent 13 in the gripping part 2b and the vibration of the circuit board 6 propagates to the entire gripping part 2b and the contact part 2a. Reference number 8 denotes a vibration transmitting part 8 for filing the gap with the housing 2 so as to prevent the loss of the vibration of the circuit board 6 in the contact part 2a (FIG. 8). The vibration transmitting part 8 is a metal member which stands up from the circuit board 6 and contact the back surface of the housing 2 to exert an elastic force and transmits high-frequency vibration of the circuit board 6 to the housing 2.

Further, on a tip end side 6a of the circuit board 6, a projection part 5b as a positioning member passes through a hole 5a (a hole for positioning) of the circuit board 6 and is fixed to the housing 2 and closed (the upper and lower ends of a positioning member 5b connects the upper side to the lower side of the housing and transmit each other's vibration.) By this positioning member 5b, the vibration loss of the circuit board which is fitted and fixed without the gap is further reduced and the vibration propagate to the housing 2.

The circuit board 6 is provided with an infrared irradiation part (infrared irradiation element) on the contact part side 6a. The infrared irradiation part (the infrared irradiation element) includes a far-infrared irradiation element 3a and a near-infrared irradiation element 3b. The infrared ray 3 is irradiated to the outside through the housing 2 having infrared transparency. In this embodiment, it is made of a synthetic resin which is transparent to a near-infrared ray, but a member having high thermal conductivity which efficiently propagates heat from a far-infrared ray to a desired part can be used. With such use, the temperature of the gums and tongue can be increased by radiant heat of far-infrared ray as conduction heat, and a cap C and the contact part 2a can be configured by a member having high thermal conductivity (heat radiation rubber and heat radiation silicone rubber), which keeps the thermal effect high. A feature of the present invention is that, out of infrared rays, the far-infrared ray is irradiated (leaked) from a transparent member (the contact part 2a and the cap C). The near-infrared ray is colorless and transparent.

Figure 5:
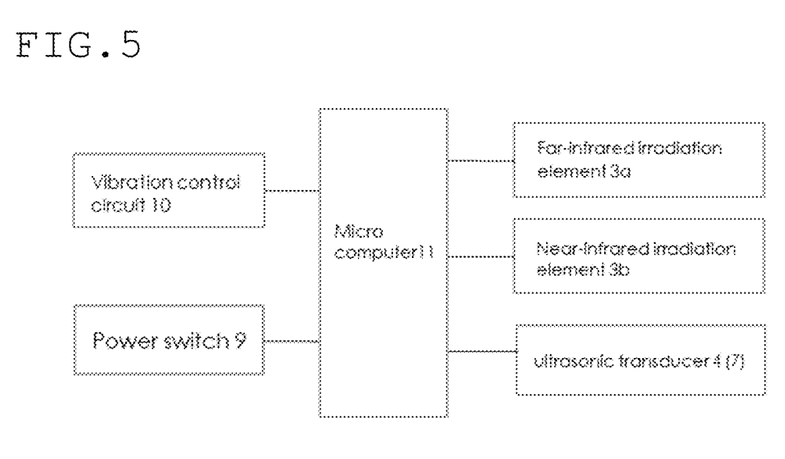
FIG. 5 is a view showing a configuration of the circuit board of the electric massage instrument according to the above first embodiment.

The far-infrared irradiation element 3a and the near-infrared irradiation element 3b are switched or simultaneously irradiated by the microcomputer 11 mounted on the circuit board (FIG. 5). In the present embodiment, the near-infrared irradiation element 3b is mounted in the longitudinal direction of the circuit board 6, and the far-infrared irradiation element 3a is mounted in a direction crossing it. Since the far-infrared irradiation element 3a and the near-infrared irradiation element 3b are alternately changed in direction (in FIGS. 4(a) and 4(b), X-X and Y-Y directions), they are also combined with the ultrasonic vibration (in FIGS. 4(a) and 4(b), X-X and Y-Y directions), the irradiation is performed to be scattered.

In the present embodiment, the contact part 2a is the rectangular shape, and the main-body part gripped with a hand is cylindrical. Although the contact part 2a is a flat part where no projections and recesses are formed in the rectangular outer peripheral side surface, the part where projections and recesses are formed (except a brush) in one side surface can be used. The recess-projection shape can be formed such that the diameter becomes smaller toward the tip end of the contact part 2a so that a stimulation can be made to the back of the oral cavity.

An ultrasonic transducer 7 which generates the ultrasonic vibration is provided on the gripping part side of the circuit board 6. Therefore, although the massage instrument 1 as a whole vibrates, the vibration is controlled by the strength of the force for gripping the gripping part 2b. Note that the infrared irradiation parts 3a and 3b also vibrate by propagating the vibration of the ultrasonic vibrator 7 through the circuit board 6, but the vibration vibrate in the X-X and Y-Y directions (FIGS. 4(a) and 4(b)).

The single circuit board 6 is narrower on the tip end side 6a than on the gripping part side 6b and is similarly fitted inside the contact part 2a having a narrow tip end side, and the vibration are transmitted to the contact part.

FIG. 5 is a view showing a configuration of the circuit board 6 of the electric massage instrument 1 of the above embodiment, and shows that it is constituted with the power switch 9, the constant voltage circuit, the lamp circuit, the high voltage generation circuit, the ultrasonic vibrator 7 and the infrared irradiation elements 3a, 3b etc.

The ultrasonic vibration element 7 is controlled by the microcomputer 11 mounted on the circuit board 6 and controlled to a predetermined frequency by the vibration control circuit 10. By this vibration control, the infrared irradiation elements 3a and 3b provided on the same circuit board are similarly controlled in vibration, and the infrared ray irradiated from the infrared irradiation part 3a and 3b are diffused by the vibration. (Vibrates in the X-X and Y-Y directions of FIGS. 4(a) and 4(b)).

When the gripping part 2b is gripped with a hand, the ultrasonic vibration 4 can be controlled by the gripping force. The microcomputer 11 performs setting and control of the ultrasonic vibration. In this embodiment, it is applied 1 to 20 times per second (1 Hz/s to 20 Hz/s) or 5 to 10 times per second (5 Hz/s to 10 Hz/s), but other settings are also possible.

Figures 6A, 6B:
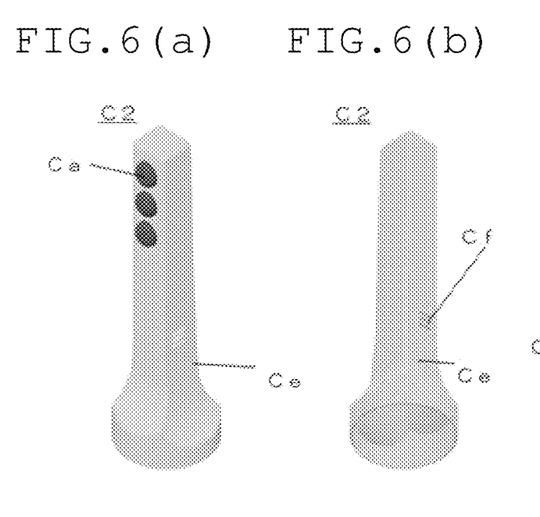
FIGS. 6(a)-6(c) are perspective views showing the cap of the electric massage instrument according to the above first embodiment.
Figure 6C:
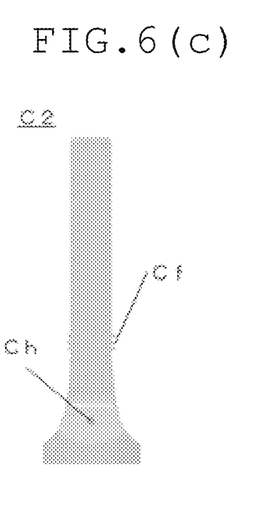

In the present embodiment, the cap C is replaced and used for the contact part 2a. The cap C is formed with a projection part Ca of a recess-projection shape (except the brush), and the cap C2 shown in FIGS. 6(a) to 6(c) has a constant thickness, and a size of a projection part Ca of the recess-projection shape (except the brush) is about 6 mm to 8 mm in diameter. Further, the base end side Ce of the cap C is formed with a hole Ch which engages with the projection part Ca provided on the base end side (the gripping part 2 (2b) side) of the contact part 2 (2a), and an anti-slip Cf when removed with a finger is provided on the opposing surface having a rectangular cross section (FIGS. 6(b) and 6(c)).

Figure 7A:
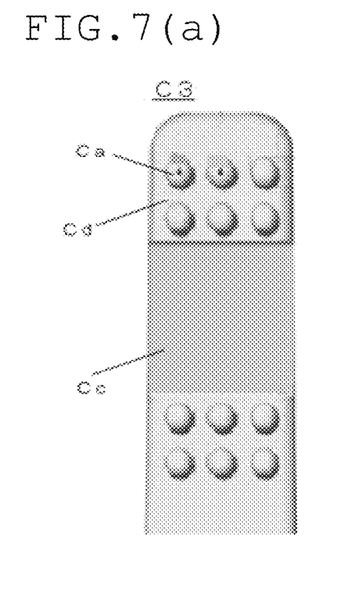
FIG. 7(a) is a front view and FIG. 7(b) is a sectional view according to the above first embodiment.
Figure 7B:
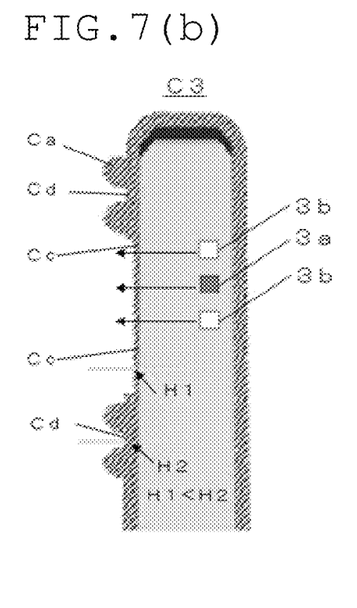

The cap C3 shown in FIGS. 7(a) and 7(b) is formed with a thin part Cc and a thick part Cd (H1<H2), and the irradiation from the infrared irradiation parts 3a and 3b is irradiated outward from the thin part Cc. Moreover, the recess-projection shape (except a brush) is formed in the thick part Cd. A size of the projection part Ca of the recess-projection shape is about 3 mm to 5 mm in diameter. Unlike a brush, if it is the recess-projection shape of this size, the effective massage can be performed by contacting a desired part not only with a surface but with a point. The configuration of the thin part Cc and the thick part Cd may be provided at a contact part of the housing.

Figure 2A:
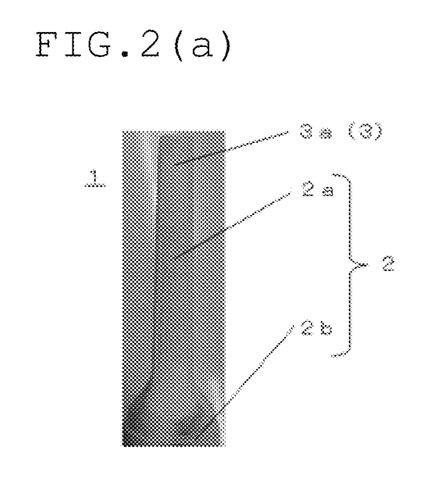
FIG. 2(a) is a view showing a contact part of the electric massage instrument and FIG. 2(b) is a view showing a state which a cap is put on according to the above embodiment of the present invention.
Figure 2B:
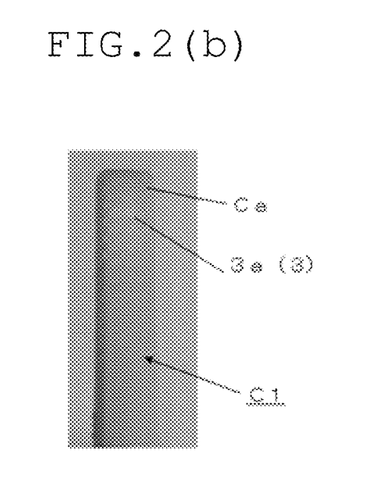
Figure 3:
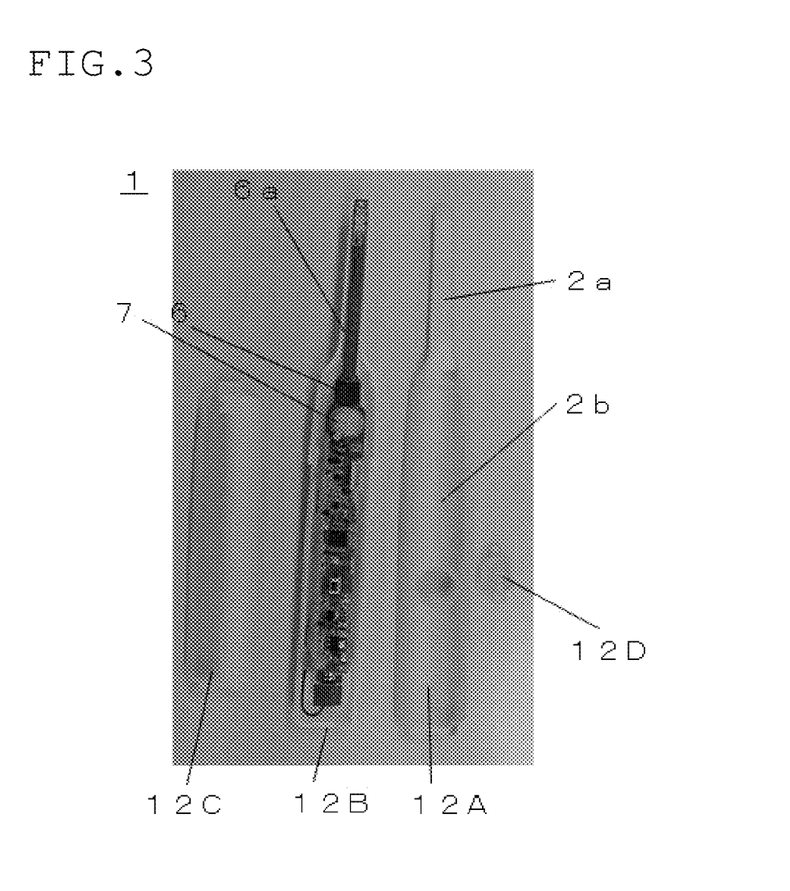
FIG. 3 is a main part structural view showing the inside of the electric massage instrument according to the above first embodiment.
Figure 4A:
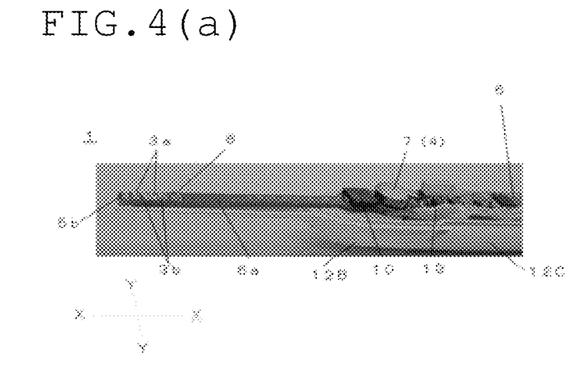
FIGS. 4(a) and 4(b) are perspective views showing a circuit board of the electric massage instrument according to the above first embodiment.
Figure 4B:
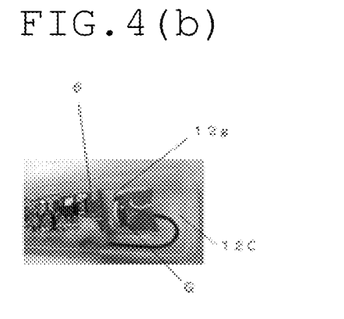

In addition, the thickness of the cap C shown in FIG. 2(b) is constant, and the size of the projection part Ca of the recess-projection shape (except the brush) is about 1 mm to 3 mm in diameter. Neither is like a brush, but is larger than the diameter of the brush, and when used in the oral cavity, it contacts the gums and tongue in a larger area than the brush.

When the electric massage instrument of the present invention is used in the oral cavity, the present inventor has obtained knowledge that the brain is activated and effective in preventing dementia, etc. by promoting the secretion of saliva. In particular, the inventor of the present application focuses on salivary secretion by stimulation of the tongue rather than stimulation of the gums and has obtained knowledge that the effect is high. For this purpose, first, the projection part Ca having a large diameter is required instead of a brush. In order to exert a massage effect in response to moisture such as saliva, it is effective to irradiate the far-infrared ray 3a to obtain a thermal effect or to irradiate the deep infrared region with the near-infrared ray 3b.

In particular, the near-infrared ray can be expected to exert anti-oxidation, antibacterial, and bad breath prevention effects in the oral cavity via saliva (the near-infrared ray with water (saliva) to promote the secretion of saliva). In addition, it activates the brain, promotes the circulation of bodily fluid and improves the circulation of extra lymph circulation. Further, the hygienic use is possible by the cap C.

In the present embodiment, a cap-like flexible material (rubber, resin, etc.) is attached around the tip end of the contact part 2*a*. The cap C has a rectangular shape, and the position of the projection part Ca of the recess-projection shape can be changed. That is, although the recess-projection shape can be set in the same direction as the direction of the infrared irradiation functions 3*a* and 3*b*, the infrared irradiation functions 3*a* and 3*b* can also irradiate by using other rectangular surfaces (surfaces without the projection part Ca of the recess-projection shape).

Therefore, when the switch 12D of the cylindrical body part of the massage instrument body 1 is turned on, the circuit board 6 and the contact part 2*a* on the tip end side vibrates, and the infrared ray are irradiated to the outside from the irradiation parts 3*a* and 3*b*. That is, the oscillation output generated from the oscillator 7 is input to the piezoelectric vibrator 7 to generate the ultrasonic vibration, and the infrared ray from the infrared ray generating elements are irradiated from the irradiation parts 3*a* and 3*b* to the outside through the transparent resin. By bringing the contact part 2*a* into contact with the gums, the gingiva and the tongue, the gums can be massaged with ultrasonic and the infrared ray. In particular, the effective massage is possible by the synergistic effect of the near-infrared ray and ultrasonic vibration. Moreover, when the cap C is put on the contact part 2*a*, the effective massage can be performed by contacting the desired part not only with the surface but also with the point by the projection part Ca of the recess-projection shape of the cap C.

The ultrasonic vibration deliver massage effects and beauty ingredients inside of the skin, improve the blood flow and lymph flow, promote the metabolism of the skin, it has a cleaning effect that removes the dirt in the pores, old keratin and the dirt accumulated in horny layer by the ultrasonic vibration.

Example 1

The amount of saliva secreted was measured by using the electric massage instrument 1 which the size of the projection part Ca of the recess-projection shape of the cap C is 1 mm to 5 mm and 2 mm to 10 mm in diameter to patients by contacting with the affected part of the oral cavity of the gums, the gingiva and the tongue. Although the secretion of saliva is promoted by stimulating the tongue, it can be said that the electric massage instrument 1 which the size of the projection part of the recess-projection shape (except the brush) is 2 mm to 10 mm in diameter is preferable.

Example 2

According to the inventor's research, the secretion of saliva needs to be performed comfortably. For this purpose, the ultrasonic vibration is applied 5 to 20 times per second (5 Hz/s to 10 Hz/s) while irradiating the near-infrared ray, and more preferably 5 to 10 times per second (5 Hz/s to 10 Hz/s).

In the experiment of the present inventor, it is most preferable that the ultrasonic vibration is about 8 times per second (8 Hz/s) while irradiating the near-infrared ray 3*b*. It can be more comfortable when irradiated at 8 times per second (8 Hz/s). Comparing a simply continuous irradiation with the irradiation at 8 Hz/s, a feeling of a user received the irradiation is different, the irradiation at 8 Hz/s makes the user comfortable and sleep. This is considered to have acted on parasympathetic nerve activation.

From these results, a preventive effect on dementia can be expected. This was also revealed in reports from the dentists who used it. It is considered that the brain is activated when the tongue is stimulated in this way. By massaging the affected part of the oral cavity with the use of this instrument 1, it is considered that an effect can be expected for patients with dementia, their spare groups, and patients with autism. In addition, as an example of use in the oral cavity, a sound wave vibration is applied from the back side of the cheek, and the spine line is pushed up easily. Finger will get tired by keeping pressing the back of mouth with finger there will be parts which are difficult to reach with finger and it will be difficult to adjust the force. However, in the present embodiment, such adjustment of the facial expression line can be easily performed.

Second Embodiment

Figure 9:
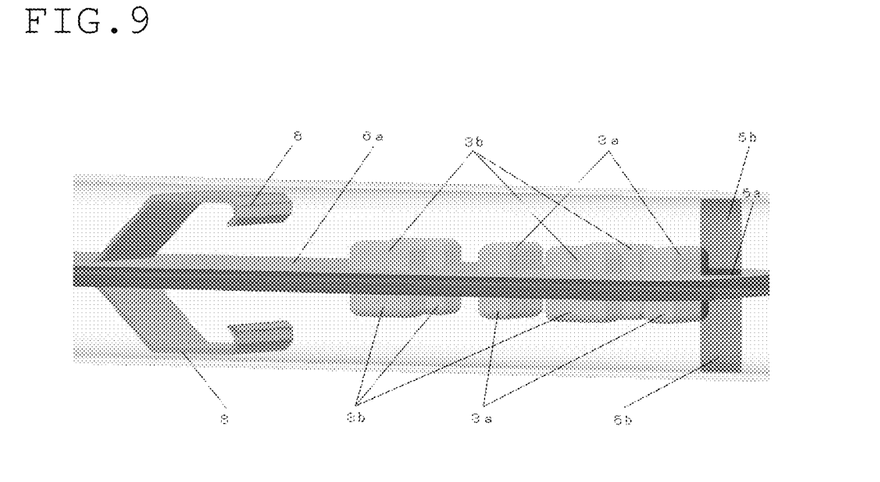
FIG. 9 is a perspective view showing a constitution of a circuit board according to the second embodiment of the present invention.

As shown in FIGS. 8 and 9, an electric massage instrument 1 of the present embodiment comprises a housing 2 which is separated into a front side and a back side and has an oval contact part 2*a* applied to an affected part, and a single circuit board 6 (extension part 6*a*) is arranged at the center. The infrared irradiation parts (the infrared irradiation elements) 3*a* and 3*b* are arranged on both front and back surfaces of the extension part 6*a*, and a vibration transmission part 8 is attached on both front and back surfaces of the extension part 6*a*. The vibration transmitting part 8 is a metal spring, is bent in a V-shape, and transmits high-frequency vibration of the circuit board 6 to the housing 2 since it connects the circuit board 6 and the inside of the housing 2 and makes elastically contact with each other by its spring.

Further, on the tip end side 6*a* of the circuit board 6, a projection part 5*b* as a positioning member passes through the hole 5*a* of the circuit board 6 and comes into contact with the back surface of the housing 2, and is closed by the other housing (the front side housing 2). The circuit board 6 transmits the ultrasonic vibration to the housing 2 at a predetermined position via the positioning member 5*b*.

The circuit board 6 is provided with an infrared irradiation part (an infrared irradiation element) on the contact part side 2*a*. The infrared irradiation part (the infrared irradiation element) includes a far-infrared irradiation element 3*a* and a near-infrared irradiation element 3*b*. The far-infrared irradiation elements 3*a* and the near-infrared irradiation elements 3*b* are arranged in the front and back of the circuit board 6, respectively. Therefore, if the contact part 2*a* is applied to the skin or the inside of the tongue and the gums in the oral cavity, the inside of the tongue and the gums can be massaged while simultaneously irradiating with the infrared ray without changing the direction.

Also, in the second embodiment, by controlling the force with which the gripping part 2*b* is gripped by hand, the vibration can be suppressed or conversely strengthened, and the infrared ray can be irradiated to be scattered by the sound wave vibration. This is because, on the contact part side 2*a*, the circuit board 6 is fitted to the housing 2, the strong vibration is transmitted to the tip side, and the vibration can be controlled by gripping the hand on the grip part side.

Figure 10A:
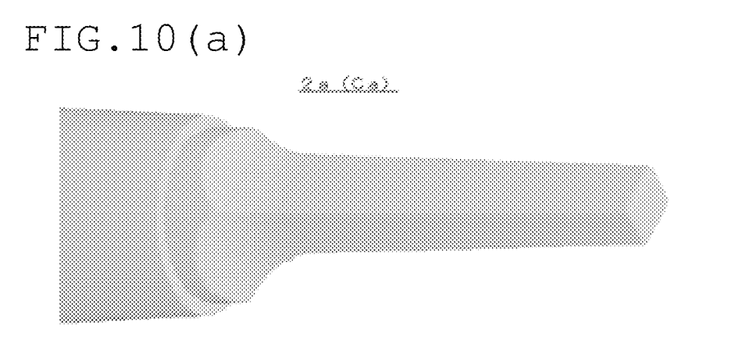
FIGS. 10(a) and 10(b) are perspective views showing types of the electric massage instrument according to the embodiment of the present invention.
Figure 10B:
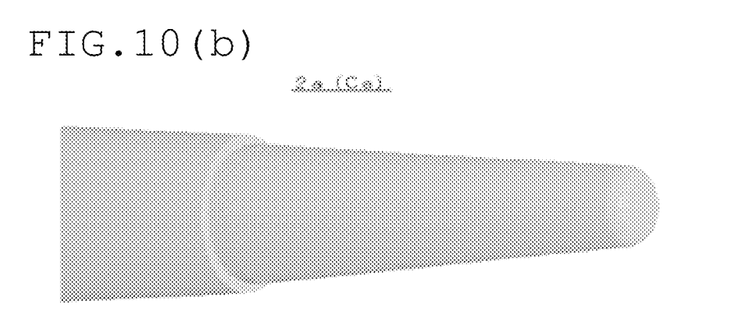

As shown in FIGS. 10(*a*) and 10(*b*), in the second embodiment, the contact part 2*a* and the cap C of the housing 2 may be rectangular, circular, or elliptical.

As described above, the housing 2 is made of synthetic resin and the cap C is made of rubber. However, the cap C may be made of flexible synthetic resin. By changing the flexibility of the material of the cap and the synthetic resin of the housing 2, it is possible to change the ultrasonic vibration, the infrared transparency, or the thickness. Thus, various modifications, variations and alternatives should be possible within the scope of the present embodiment.

REFERENCE NUMERALS 1 electric massage instrument
2 housing, 2a contact part, 2b gripping part
3 infrared irradiation function
3a,3b infrared irradiation elements (infrared irradiation parts)
3a far-infrared irradiation element
3b near-infrared irradiation element
4 ultrasonic vibration function
5a hole, 5b projection part as a positioning member
6 circuit board, 6a tip end side (contact part side)
7 ultrasonic transducer
8 vibration transmitting part
9 power switch
10 vibration control circuit
11 microcomputer
12g battery housing part
13 adhesive agent
G battery
C cap
Ca projection part, Cc thin part, Cd thick part

The invention claimed is:

1. An electric massage instrument, comprising:
a gripping portion, and a contact portion extending from the gripping portion, and
a circuit board disposed in the gripping portion and the contact portion, and including an electronic circuit having an ultrasonic vibration device to provide ultrasonic vibration and an infrared ray irradiation device to provide infrared ray, the infrared ray irradiation device having an irradiation portion extending from the circuit board and provided on a tip end side of the contact portion,
wherein the contact portion is made of a member having infrared ray transparency and/or is provided with a cap which covers the contact portion and is made of a member having infrared ray transparency,
the infrared ray irradiation device provides a far-infrared ray and a near-infrared ray, and
the circuit board is provided with a switch which irradiates the far-infrared ray and the near-infrared ray simultaneously or individually.

2. An electric massage instrument, comprising:
a gripping portion, and a contact portion extending from the gripping portion, and
a circuit board disposed in the gripping portion and the contact portion, and including an electronic circuit having an ultrasonic vibration device to provide ultrasonic vibration and an infrared ray irradiation device to provide infrared ray, the infrared ray irradiation device having an irradiation portion extending from the circuit board and provided on a tip end side of the contact portion,
wherein the contact portion is made of a member having infrared ray transparency and/or is provided with a cap which covers the contact portion and is made of a member having infrared ray transparency,
the contact portion or the cap is formed with a recess-projection portion made of rubber or synthetic resin,
the infrared ray irradiation device irradiates the infrared ray toward the recess-projection portion made of rubber, and
the tip end side includes far-infrared ray irradiation portions and near-infrared ray irradiation portions between the far-infrared ray irradiation portions, or the far-infrared ray irradiation portions are provided such that directions thereof are alternately changed.

3. An electric massage instrument comprising:
a gripping portion, and a contact portion extending from the gripping portion, and
a circuit board disposed in the gripping portion and the contact portion, and including an electronic circuit having an ultrasonic vibration device to provide ultrasonic vibration and an infrared ray irradiation device to provide infrared ray, the infrared ray irradiation device having an irradiation portion extending from the circuit board and provided on a tip end side of the contact portion, the irradiation portion irradiating a far-infrared ray and a near-infrared ray,
wherein the contact portion is made of a member having infrared ray transparency and/or is provided with a cap which covers the contact portion and is made of a member having infrared ray transparency, and
the contact portion and/or cape is formed with a first portion and a second portion thinner than the first portion, and a recess-projection portion is not formed on the second portion, and far-infrared ray irradiation portions and near-infrared ray irradiation portions are irradiated toward the second portion.

4. The electric massage instrument according to claim 1, wherein
the gripping portion and the contact portion form a housing,
the circuit board is a single circuit board extending from the gripping portion into the contact portion, and
an ultrasonic transducer as the ultrasonic vibration device is provided on a side of the gripping portion.

* * * * *